(12) United States Patent
Victor et al.

(10) Patent No.: US 10,293,065 B2
(45) Date of Patent: May 21, 2019

(54) OPTICAL FIBER BASED ANTIMICROBIAL ULTRAVIOLET RADIATION THERAPY SYSTEM

(71) Applicant: TELEFLEX MEDICAL INCORPORATED, Research Triangle Park, NC (US)

(72) Inventors: John C. Victor, Kunkletown, PA (US); David Troy Rowe, Sinking Spring, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 667 days.

(21) Appl. No.: 14/775,562

(22) PCT Filed: Mar. 13, 2014

(86) PCT No.: PCT/US2014/025371
§ 371 (c)(1),
(2) Date: Sep. 11, 2015

(87) PCT Pub. No.: WO2014/159874
PCT Pub. Date: Oct. 2, 2014

(65) Prior Publication Data
US 2016/0038621 A1 Feb. 11, 2016

Related U.S. Application Data

(60) Provisional application No. 61/783,095, filed on Mar. 14, 2013.

(51) Int. Cl.
*A61M 16/00* (2006.01)
*A61L 2/10* (2006.01)
(Continued)

(52) U.S. Cl.
CPC .............. *A61L 2/10* (2013.01); *A61L 2/00* (2013.01); *A61M 16/04* (2013.01);
(Continued)

(58) Field of Classification Search
CPC .......... A61L 2/10; A61L 2/00; A61L 2202/24; A61L 2202/15; A61M 16/04;
(Continued)

(56) References Cited

U.S. PATENT DOCUMENTS 5,207,669 A * 5/1993 Baker ................. A61B 18/245
606/15
5,260,020 A 11/1993 Wilk et al.
(Continued)

FOREIGN PATENT DOCUMENTS

JP 47-42534 A 12/1972
JP 4-156939 A 5/1992
(Continued)

OTHER PUBLICATIONS

Japanese Office Action dated Jan. 10, 2017, in Japanese Patent Application No. 2016-501838.
(Continued)

*Primary Examiner* — Steven O Douglas
(74) *Attorney, Agent, or Firm* — Baker & Hostetler LLP (57) ABSTRACT

An ultraviolet irradiation system includes a medical device having a central lumen, an optical fiber having a longitudinal length, and an ultraviolet wave generator, wherein ultraviolet waves generated by the wave generator are dispersed along the longitudinal length of the optical fiber to disinfect the central lumen of the medical device.

16 Claims, 8 Drawing Sheets

(51) Int. Cl.
*A61L 2/00* (2006.01)
*A61M 16/04* (2006.01)
*A61M 25/00* (2006.01)
*A61M 25/01* (2006.01)
*G02B 6/00* (2006.01)
*A61N 5/06* (2006.01)

(52) U.S. Cl.
CPC .... *A61M 16/0402* (2014.02); *A61M 25/0017* (2013.01); *A61M 25/0102* (2013.01); *A61L 2202/15* (2013.01); *A61L 2202/24* (2013.01); *A61M 16/0434* (2013.01); *A61M 2205/053* (2013.01); *A61M 2209/10* (2013.01); *A61N 2005/063* (2013.01); *G02B 6/00* (2013.01)

(58) Field of Classification Search
CPC .......... A61M 16/0402; A61M 25/0102; A61M 25/0017; A61M 16/0434; A61M 2209/10; A61M 2205/053; A61N 2005/063; G02B 6/00
See application file for complete search history.

(56) References Cited

U.S. PATENT DOCUMENTS

| | | | |
|---|---|---|---|
| 5,334,171 A * | 8/1994 | Kaldany | A61L 29/042 604/20 |
| 5,695,482 A | 12/1997 | Kaldany | |
| 5,855,203 A * | 1/1999 | Matter | A61L 2/10 128/207.14 |
| 6,004,315 A | 12/1999 | Dumont | |
| 6,461,569 B1 | 10/2002 | Boudreaux | |
| 7,159,590 B2 * | 1/2007 | Rife | A61M 16/04 128/200.26 |
| 8,235,916 B2 * | 8/2012 | Whiting | A61B 17/3468 128/898 |
| 9,808,647 B2 * | 11/2017 | Rhodes | A61N 5/0624 |
| 2001/0016176 A1 | 8/2001 | Lin et al. | |
| 2007/0187626 A1 | 8/2007 | Gaska et al. | |
| 2008/0257355 A1 * | 10/2008 | Rao | A61L 2/10 128/207.14 |
| 2010/0036410 A1 | 2/2010 | Krolik et al. | |
| 2010/0114303 A1 * | 5/2010 | Su | A61F 2/0077 623/1.46 |
| 2011/0085936 A1 | 4/2011 | Haytman et al. | |
| 2011/0152789 A1 | 6/2011 | Dacey, Jr. | |
| 2011/0213339 A1 | 9/2011 | Bak | |
| 2012/0321509 A1 | 12/2012 | Bak | |
| 2013/0060188 A1 | 3/2013 | Bedwell | |
| 2016/0317832 A1 * | 11/2016 | Barneck | A61N 5/0603 |

FOREIGN PATENT DOCUMENTS

| | | |
|---|---|---|
| JP | 6-62691 A | 3/1994 |
| JP | 6-63106 A | 3/1994 |
| JP | 7-198953 A | 8/1995 |
| JP | 8-215316 A | 8/1996 |
| JP | 9-506716 A | 6/1997 |
| JP | 2001-502438 A | 2/2001 |
| JP | 2005-13723 A | 1/2005 |
| JP | 2009-90093 A | 4/2009 |
| WO | 00/79319 A1 | 12/2000 |
| WO | 2012177803 A1 | 12/2012 |

OTHER PUBLICATIONS

Decision of Grant issued in Japanese Application No. 2017-157563, dated Feb. 4, 2019.

* cited by examiner

OPTICAL FIBER BASED ANTIMICROBIAL ULTRAVIOLET RADIATION THERAPY SYSTEM

CROSS-REFERENCE TO RELATED APPLICATIONS

This application is a National Stage of International patent application PCT/US2014/025371, filed on Mar. 13, 2014, which claims priority to U.S. provisional patent application No. 61/783,095, filed on Mar. 14, 2013, the disclosures of which are incorporated by reference in their entirety.

FIELD OF THE INVENTION

The invention generally relates to ultraviolet irradiation systems, and, more particularly, to methods and systems for delivering an irradiating light source through a side emission delivery fiber.

BACKGROUND OF THE INVENTION

The current paradigm for reducing device related incidence of catheter-related bloodstream infections (CRBSI), ventilator associated pneumonia (VAP), and urinary tract infections (UTI) utilizes drug or chemical eluding agents that are incorporated into or coated onto the devices used in these procedures. Due to their extensive utilization, many of the antimicrobial and antiseptic drugs used with these devices are showing an increasing incidence of hypersensitivity reactions as well as presensitization within the general population.

A need exists for methods and systems that offer advantages to conventional infection control approaches while retaining or enhancing antimicrobial efficacy and extending device patency.

SUMMARY OF THE INVENTION

The foregoing needs are met by the present invention, wherein according to certain aspects, an ultraviolet irradiation system includes a medical device having a central lumen, an optical fiber having a longitudinal length, and an ultraviolet wave generator, wherein ultraviolet waves generated by the wave generator are dispersed along the longitudinal length of the optical fiber to disinfect the central lumen of the medical device.

In accordance with other aspects of the present invention, the medical device includes a cylindrical wall surrounding the central lumen, and the optical fiber is embedded into the wall.

In accordance with yet other aspects of the present invention, the optical fiber is embedded into the wall in a helical pattern. The optical fiber may further include a cylindrical core and a cladding layer, the cladding layer having a varied thickness over the longitudinal length. The core may comprise a PMMA material extruded with a specific proportion of scattering particles compounded into the PMMA material.

In accordance with other aspects of the present invention, surface pitting and solvent voids may be formed in the cladding layer by a chemical abrasion process. In accordance with yet other aspects of the present invention, surface pores may be formed in the cladding layer by a micro abrasion process. Facets in the core may be formed by the micro abrasion process.

In accordance with other aspects of the present invention, the medical device may include an endotracheal tube, a central venous catheter stylet or a foley catheter stylet.

In accordance with other aspects of the present invention, the ultraviolet waves generated by the wave generator may be uniformly emitted along the longitudinal length of the optical fiber.

There has thus been outlined, rather broadly, certain aspects of the present disclosure in order that the detailed description herein may be better understood, and in order that the present contribution to the art may be better appreciated.

In this respect, before explaining at least one embodiment of the invention in detail, it is to be understood that the invention is not limited in its application to the details of the construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Ultraviolet light is a highly potent antiseptic and antimicrobial agent. Although most commonly used for sterilization of surfaces, air and water systems, light irradiation may be used as an infection control mechanism in a wide array of disposable in-dwelling and ex-vivo medical devices and disposable materials.

Ultraviolet irradiation offers several unique advantages for medical device infection control. Ultraviolet irradiation can be easily and completely controlled and it is not dependent on materials or manufacturing process variation. The mechanism of action of the irradiation energy is the direct disruption of molecular bonds within the organism's genetic material. Molecular bond energy is typically expressed in units of eV (Electron Volts) and the photonic energy of light is the product of its frequency multiplied by Plank's constant (~6.63×10^×34 m^2*Kg/Sec). Specific organisms can be targeted by adjusting the intensity and frequency of the ultraviolet irradiation. In addition, in vitro experiments have demonstrated a significant safety margin between microbe eradication dose levels and safe human endothelial cell exposures. Moreover, the effectiveness of ultraviolet irradiation as an antimicrobial agent does not diminish in long term indwelling applications.

A relatively narrow band source of light may be used in the irradiation devices described herein. For example, the frequency bandwidth of ~10 nm with a spectral peak at 366 nm may be used due to a combination of Poly(methyl methacrylate) or PMMA transmissivity, cost, availability and antimicrobial efficacy. This peak frequency corresponds to an energy value range of 3.5-3.6 eV which is also the disruption energy associated with the S—H and C—C (Sulfur-Hydrogen and Carbon-Carbon) molecular covalent bonds within the organisms genetic material. The theoretical eradication dose level for *Staphylococcus Aureus* (SA) bacteria is ~2.3 J/cm$^2$. This value corresponds to an optical energy fluence value of ~80 uW/cm$^2$ for an 8 hour therapeutic exposure over the surface of the fiber. Experimentally, significantly lower optical fluence values have shown complete inhibition in 7 log inoculums of several species, including SA. This may be attributable to the integration of energies associated with the full spectral band of the irradiation source.

The primary components of an ultraviolet irradiation system in accordance with aspects of the present invention are a controllable programmable UV light source, a side emission delivery fiber, and coupling optics to efficiently launch source energy into the delivery fiber. The combination of these components as described herein provides ultraviolet delivery and irradiation into medical devices as an antimicrobial mechanism.

Figure 1:
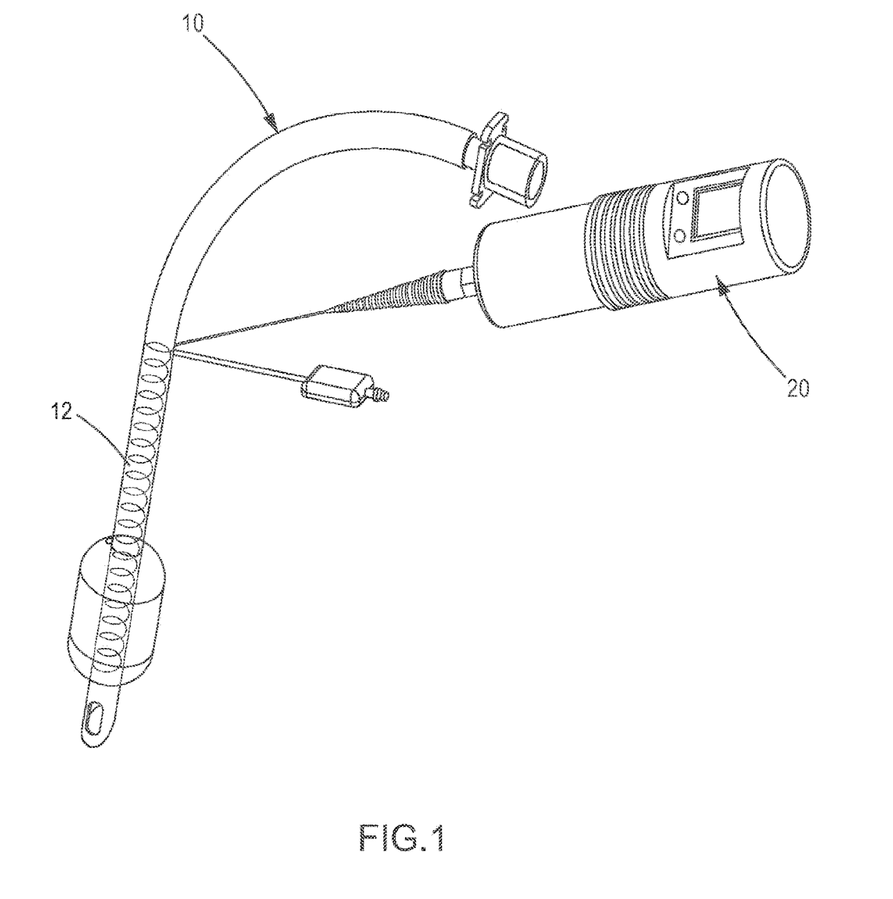
FIG. 1 illustrates an endotracheal tube incorporating a helical side emission fiber and controllable light source, in accordance with aspects of the present disclosure.

FIG. 1 illustrates an antimicrobial photonic (AMP) endotracheal tube (ETT) 10 having an embedded fiber helix 12. The fiber helix 12 may be a spirally formed plastic optical fiber (PMMA) and configured as a molded structure on the surface of the ETT 10, which may be made of a thermoplastic material, such as polyvinyl chloride (PVC). High efficiency ultraviolet side emission is gained by adjusting the helical curvature (pitch) to exceed the optical angle of total internal reflection. Additionally, to compensate for reduced optical power from distal to proximal tube ends, the helical pitch is varied to achieve uniform irradiation over the device length. The fiber helix 12 is a permanent and integral part of the ETT 10.

The manufacturing process involves pre-forming of the optical fiber (heating and dwelling at glassification temperatures) over a mandrel (pitch guide). This technique relieves stress within the fiber and facilitates the solvent based PVC over-molding process. A proximal end of the fiber may be mirrored by metallic sputter deposition to increase overall emission efficiency and a distal end may be strain relieved and terminated with a low cost optical connector. A programmable light source 20 may be used to generate the ultraviolet radiation using either a single or multiple element non-coherent light emitting diodes (LED) array. LED power may be supplied from a constant current source that can be programmed for specific power levels, "on" durations, or repetitive dose regiments.

Figure 2:
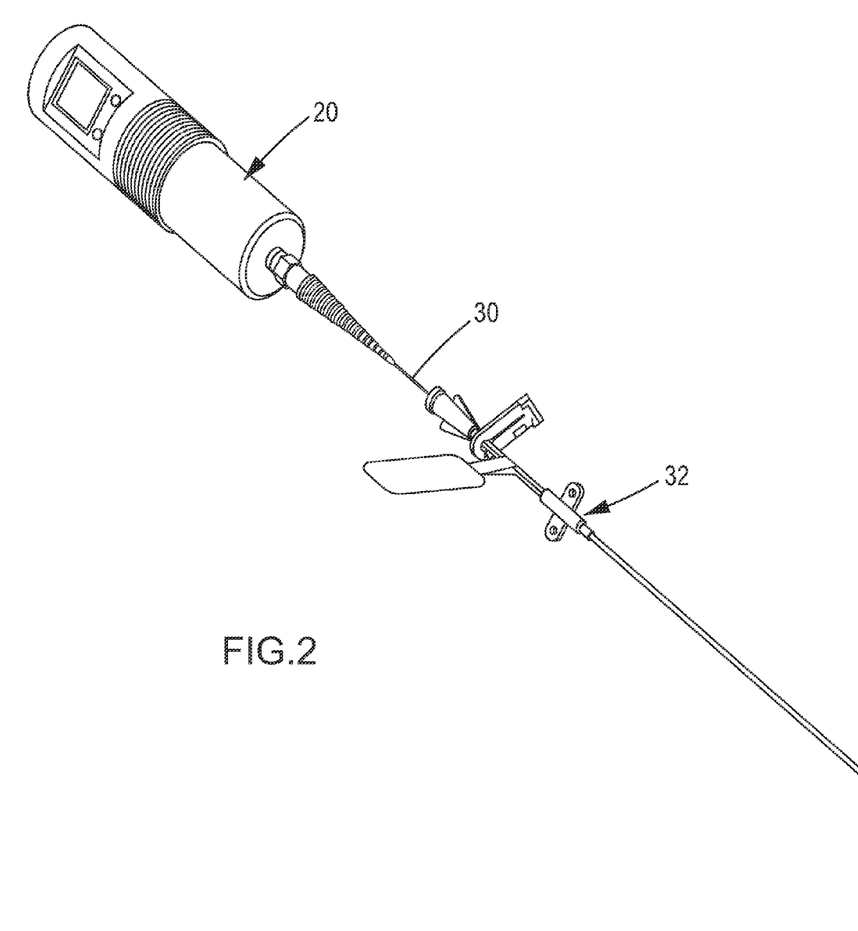
FIG. 2 illustrates an antimicrobial photonic central venous catheter stylet, in accordance with aspects of the present disclosure.

FIG. 2 illustrates an AMP central venous catheter (CVC) stylet 30. The stylet 30 incorporates a length of plastic optical fiber (PMMA) as a stylet to be inserted into a CVC lumen 32. High efficiency ultraviolet side emission may be gained by a combination of chemical solvent and/or mechanical etching of the fiber clad material of the stylet to disrupt the evanescent field. In addition, optical scattering nano-particles may be added to the clad, and the addition of nano-particles to the PMMA core material may also be used to enhance the efficiency of side emissions by altering the distribution of light within the fiber. Additionally, to compensate for reduced optical power along the fiber length, the emission enhancing process can be varied to achieve uniform irradiation along the entire stylet 30. For example, compensation for optical power variation may be achieved by a "Bump" extrusion process where the diameter of the fiber is varied over a specific length. This approach enhances side emission efficiency of the stylet 30 by a corresponding increase in the numerical aperture (NA) of the fiber as the diameter diminishes.

The fiber stylet 30 may be an independent disposable element that may either be included in a CVC kit or provided separately as needed. The manufacturing process involves a rate controlled exposure of the fiber to an etching medium containing a dispersion of scattering particles. Alternatively, the base PMMA fiber core may be extruded with a specific proportion of scattering particles compounded into the base material. The proximal end of the fiber stylet 30 may be mirrored by metallic sputter deposition to increase overall emission efficiency and the distal end of the fiber stylet 30 may be strain relieved and terminated with a low cost optical connector. The stylet 30 may be introduced into a saline charged CVC lumen 32, for example, by way of Tuohy Borst adapter attached to the luer fitting of an extension line. This connectivity facilitates access to the CVC lumen while preventing luminal fluid discharge.

Figure 3:
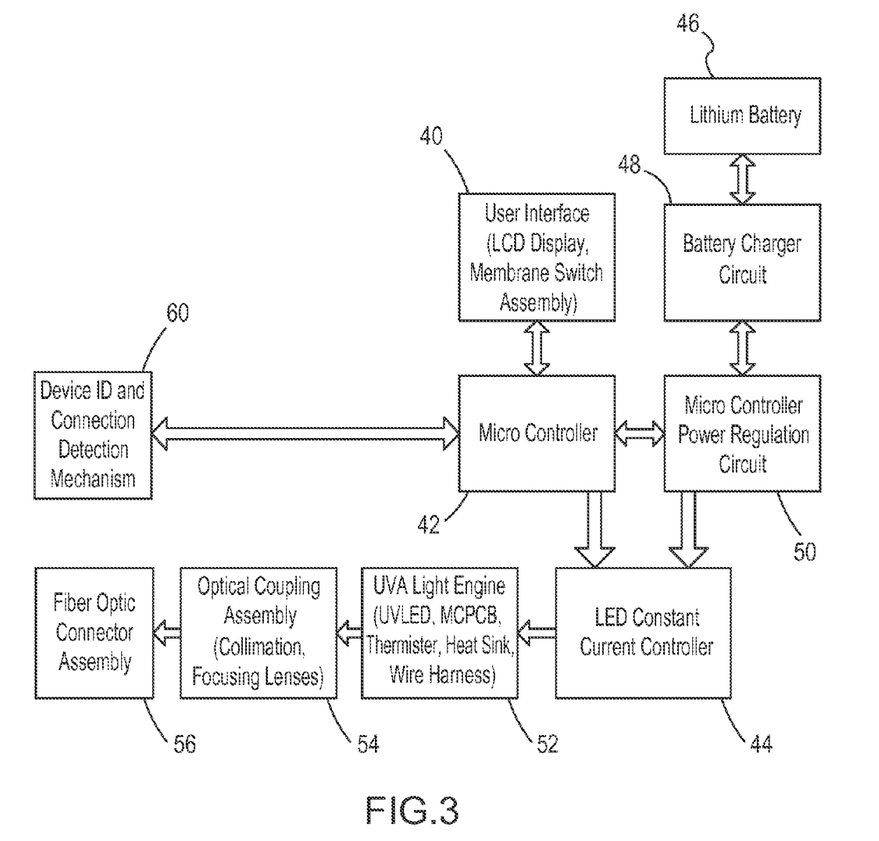
FIG. 3 illustrates functional features of a programmable controllable light source, in accordance with aspects of the present disclosure.

A programmable light source 20 may be used to generate the ultraviolet radiation in the stylet 30 using either a single or multiple element non-coherent light emitting diodes (LED) array. FIG. 3 shows a functional block diagram for a programmable light source 20 in accordance with aspects of the present invention. The light source 20 may have a user interface 40 that includes a liquid crystal display (LCD) and a switch assembly for control of the programmable light source 20. A microcontroller 42 may respond to input from the user interface to control the LED constant current controller 44. For example, the user interface 40 may be used to program the programmable light source for specific power levels, "on" durations, or repetitive dose regiments. A power source, such as a lithium battery 46, a battery charger circuit 48 and a power regulation circuit 50 may be included to generate and regulate power for the constant current controller 44 in order to provide a constant current to the ultraviolet light engine 52. The ultraviolet radiation generated by the ultraviolet LEDs in the light engine 52 are delivered through an optic coupling assembly 54, which may include focusing lenses for collimation of the ultraviolet light delivered to the fiber optic connector assembly 56. A device identification and connection detection mechanism

60 may be provided to provide a signal to the user interface 40 when the light source 20 is properly connected via the fiber optic connector assembly 56 to a side emission light fiber.

In accordance with yet other aspects of the present invention, an AMP foley catheter stylet may be similarly formed by incorporating a length of plastic optical fiber (PMMA) as a stylet to be inserted into a catheter lumen. High efficiency ultraviolet side emission may be gained by a combination of chemical solvent and/or mechanical etching of the fiber clad material to disrupt the evanescent field. The addition of optical scattering nano-particles to the clad, and the addition of nano-particles to the PMMA core material may be used to enhance the efficiency of side emissions by altering the distribution of light within the fiber. Compensation for optical power variation may also be achieved by a "Bump" extrusion process where the diameter of the fiber is varied over a specific length. This approach enhances side emission efficiency by a corresponding increase in the numerical aperture (NA) of the fiber as the diameter diminishes.

The fiber stylet may be an independent disposable element that may either be included in a Foley package or provided separately as needed. The manufacturing process of the Foley catheter stylet involves a rate controlled exposure of the fiber to an etching medium containing a dispersion of scattering particles. Alternatively, the base PMMA fiber core may be extruded with a specific proportion of scattering particles compounded into the base material. The proximal end of the fiber may be mirrored by metallic sputter deposition to increase overall emission efficiency and the distal end may be strain relieved and terminated with a low cost optical connector.

The stylet may be introduced into the Foley catheter by a modified Tuohy Borst adapter attached to the port of a secondary lumen or by way of a secondary access port to the Foley central lumen. This connectivity facilitates irradiation of the central Foley catheter lumen while permitting normal urine drainage and collection bag attachment.

A programmable light source 20 may be used to generate the ultraviolet radiation in the Foley catheter stylet by using either a single or multiple element non-coherent light emitting diodes (LED) array. LED power may be supplied from a constant current source that can be programmed for specific power levels, "on" durations, or repetitive dose regiments.

In accordance with other aspects of the present disclosure, an AMP Foley catheter or a Urethane Chronic Hemodialysis catheter, for example, may include an embedded side emission fiber. The catheters may incorporate a length of plastic optical fiber (PMMA) permanently into either the webbing structure or a dedicated lumen of the catheters. High efficiency ultraviolet side emission may be gained by a combination of chemical solvent and/or mechanical etching of the fiber clad material to disrupt the evanescent field. The addition of optical scattering nano-particles to the clad, and the addition of nano-particles to the PMMA core material may also be used to enhance the efficiency of side emissions by altering the distribution of light within the fiber. Additionally, to compensate for reduced optical power along the fiber length, the emission enhancing process can be varied to achieve uniform irradiation along the entire fiber.

Compensation for optical power variation may also be achieved by a "Bump" extrusion process where the diameter of the fiber is varied over a specific length. This approach enhances side emission efficiency by a corresponding increase in the numerical aperture (NA) of the fiber as the diameter diminishes. The manufacturing process involves a rate controlled exposure of the fiber to an etching medium containing a dispersion of scattering particles. Alternatively, the base PMMA fiber core may be extruded with a specific proportion of scattering particles compounded into the base material. The proximal end of the fiber may be mirrored by metallic sputter deposition to increase overall emission efficiency and the distal end may be strain relieved and terminated with a low cost optical connector.

A programmable light source 20 may be used to generate the ultraviolet radiation in the embedded fiber Foley catheter using either a single or multiple element non-coherent light emitting diodes (LED) array. LED power may be supplied from a constant current source that can be programmed for specific power levels, "on" durations, or repetitive dose regiments.

Figure 4:
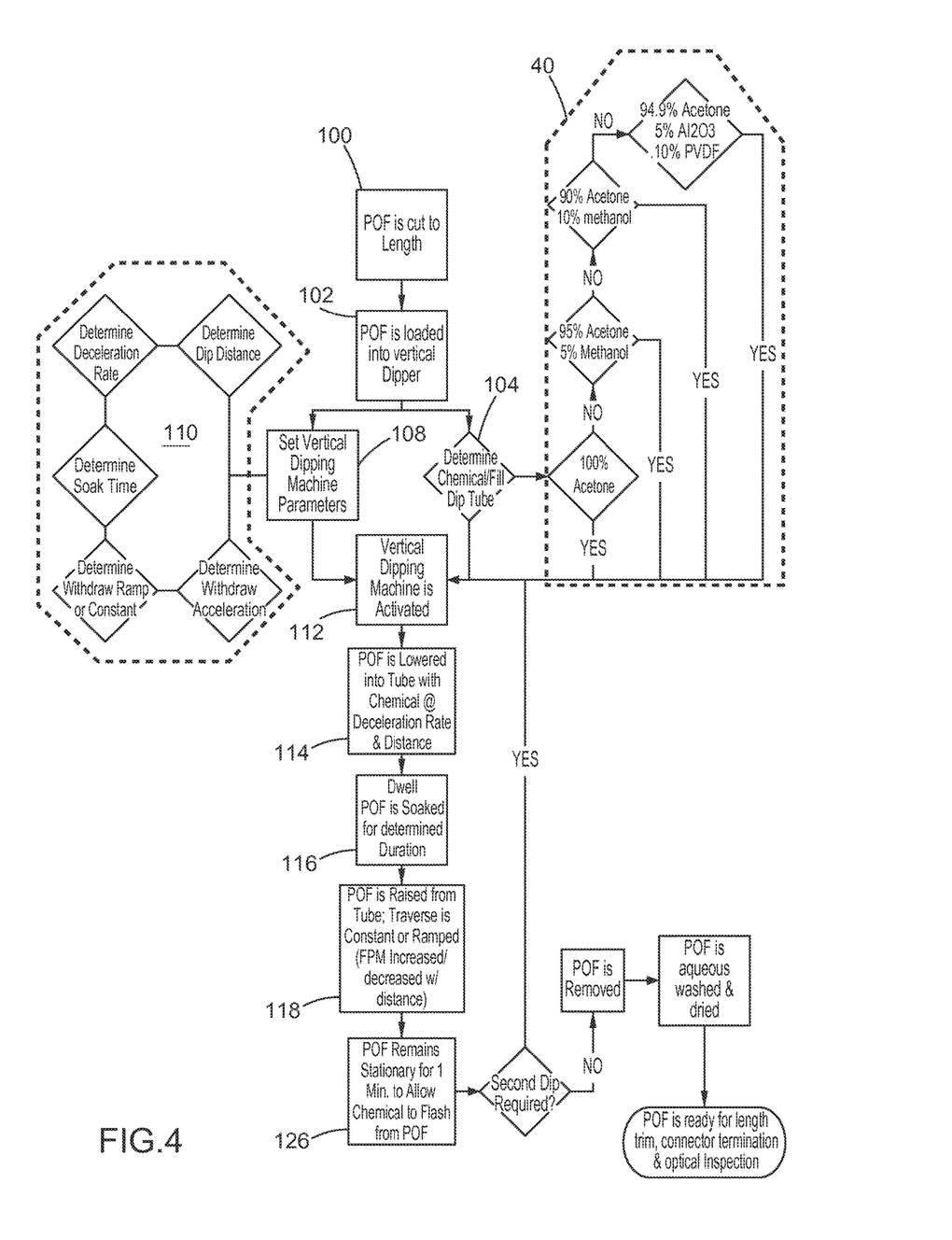
FIG. 4 illustrates a chemical abrasion process flow for forming a side emission fiber, in accordance with aspects of the present disclosure.

FIG. 4 illustrates a chemical abrasion process flow for forming a side emission optical fiber configured for use in the systems and devices described above. A piece of polymer optical fiber (POF) is first cut to a predetermined length at step 100 and then loaded into a vertical dipper at step 102. The POF may be configured to have a core layer made of a suitable material, such as PMMA or polystyrene, with higher refractive indices of 1.49 and 1.59 respectively. A cladding layer may be provided made of a silicone resin, or a fluorinated polymer or perfluorinated polymer, for example, having a lower refractive index of approximately 1.46.

At step 104, the chemical to be used is determined and the dip tube filled. As shown, the component content of the chemical may be derived through a series of checks at step 106 in which it is determined whether the chemical comprises, for example, 100% acetone, a 95% acetone and 5% methanol mix, a 90% acetone and 10% methanol mix, or a 94.9% acetone, 5% aluminum carbonate ($Al_2O_3$), and 0.1% polyvinylidene fluoride (PVDF) mix.

Figure 5:
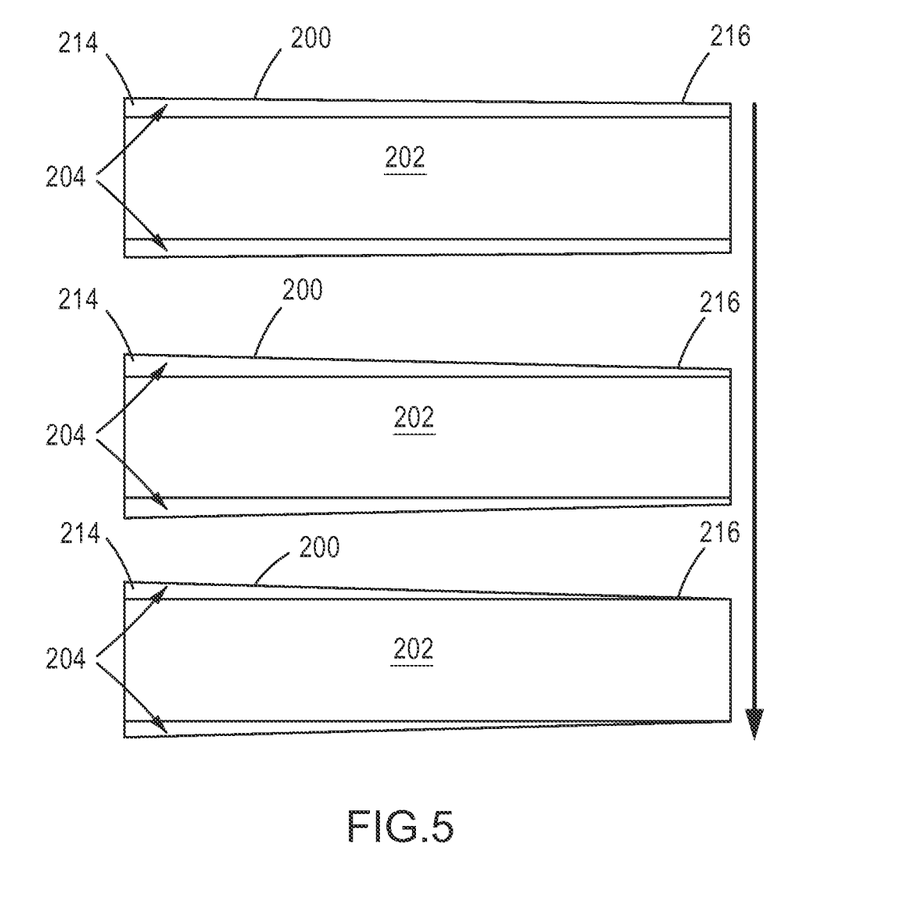
FIG. 5 illustrates various stages of a polymer optical fiber subjected to the chemical abrasion process, in accordance with aspects of the present disclosure.

At step 108 a number of parameters are determined and set for operation of the vertical dipping machine, including, for example, those shown at 110, which include determining dip distance, deceleration rate, soak time, withdraw ramp or constant, and withdraw acceleration. With the dip tube filled with an appropriate chemical determined at 104 and the parameters set at step 108, the vertical dipping machine is activated at step 112. At step 114, the POF is lowered into the dip tube filled with the chemical at the determined deceleration rate and distance. At step 116, the POF is soaked for the predetermined soak time duration. At step 118, the POF is raised from the dip tube. Depending on whether the traverse is determined to be constant or ramped, the rate at which the POF is withdrawn from the chemical bath may be increased or decreased. The acetone removes the POF cladding while also creating micro porosity within the cladding that remains. The rate of cladding removal and porosity size in the cladding are dependent on the dipping machine parameters determined in step 108. For example, the soak time and/or the POF withdraw rate from the chemical directly impact the final cladding thickness and porosity. Accordingly, the rate of acceleration from the chemical bath may be used to taper the cladding thickness from a proximal to distal end of the POF in addition to creating porosity variation. For example, FIG. 5 is a cross-sectional view of a POF 200 illustrating the core 202 and cladding 204 from a proximal end 214 to a distal end 216. The same POF 200 is shown three times to illustrate the impact of an increased soak time and/or decreased rate of withdraw on a thickness of the cladding 204. As illustrated by the arrow on the right, with increased soak time and/or a decrease in the rate of withdraw, the cladding thickness decreases and depth of porosity increases from the proximal end 214 to distal end 216 of the POF 200.

Referring back to FIG. 4, with the POF withdrawn from the dipping tube, the POF may be held stationary at step 120 for a predetermined amount of time, such as 1 minute, to allow the chemical to evaporate from the POF. At step 122, a determination is made whether to perform a repeat dip of the POF. The dipping process described above may be performed again. If a repeat dip is not necessary, the POF may be removed from the dipping machine at step 124. At step 126, the POF is washed in an aqueous bath and dried. As shown in step 128, the washed and dried POF may be trimmed to a desired length. Optical fiber connectors, which may be FC, SC, ST, LC, MTRJ, or SMA type connectors, may be configured onto the POF. The side emission fiber may then undergo an optical inspection prior to being used as described above in one of the various devices.

Figure 6:
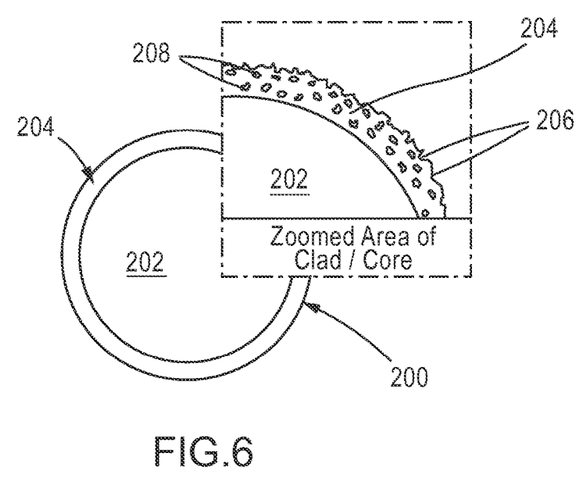
FIG. 6 shows a cross-sectional view of a polymer optical fiber and a close-up view of a portion of the cladding, in accordance with aspects of the present disclosure.
Figure 7:
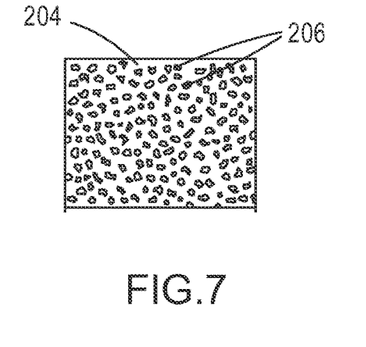
FIG. 7 is a close-up surface view of the polymer optical fiber shown in FIG. 6, in accordance with aspects of the present disclosure.

FIGS. 6 and 7 illustrate aspects of a POF 200 chemically abraded with an acetone solvent in accordance with the process described above. FIG. 6 is a cross-sectional view of the POF 200 illustrating the core 202 and cladding 204. A zoomed portion of the cladding 204 is shown to illustrate the surface pitting 206 and voids 208 that are formed as a result of the chemical abrasion process. FIG. 7 illustrates a surface view of a portion of the cladding 204 with surface pitting 206. The amount of surface pitting 206 and voids 204 may be closely controlled by the parameters set forth in the dipping machine during the abrasion process. The pitting 206 and voids 204 in the POF enhance the dispersion of the ultraviolet radiation through side emission.

Figure 8:
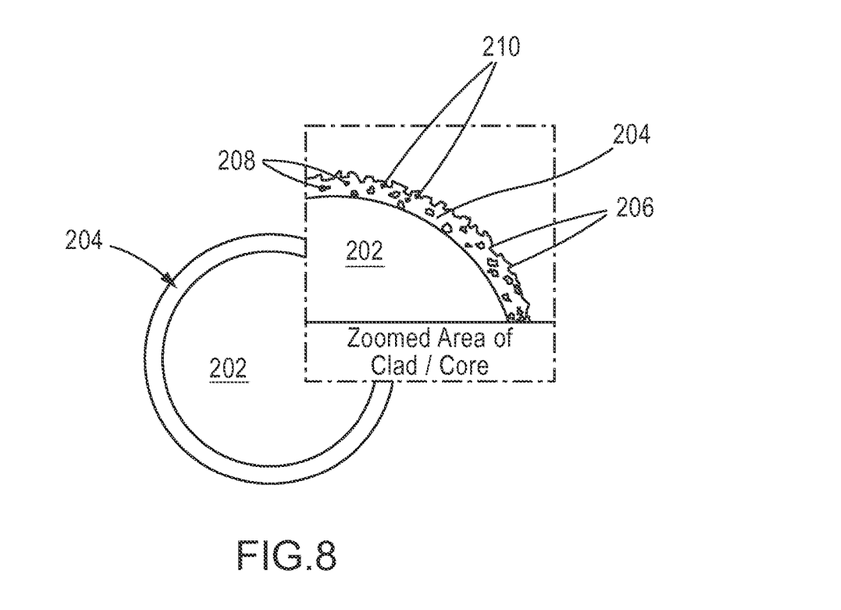
FIG. 8 shows a cross-sectional view of a polymer optical fiber and a close-up view of a portion of the cladding, in accordance with aspects of the present disclosure.

In accordance with other aspects of the present invention, the acetone solvent may be mixed with a particulate compound, such as aluminum carbonate. As shown in FIG. 8, the aluminum carbonate particles 210 become embedded in the cladding 204 during the abrasion process. In combination with the surface pitting 206 and voids 204 generated by the acetone, the embedded particles 210 may further enhance side emission of the ultraviolet radiation.

Figure 9:
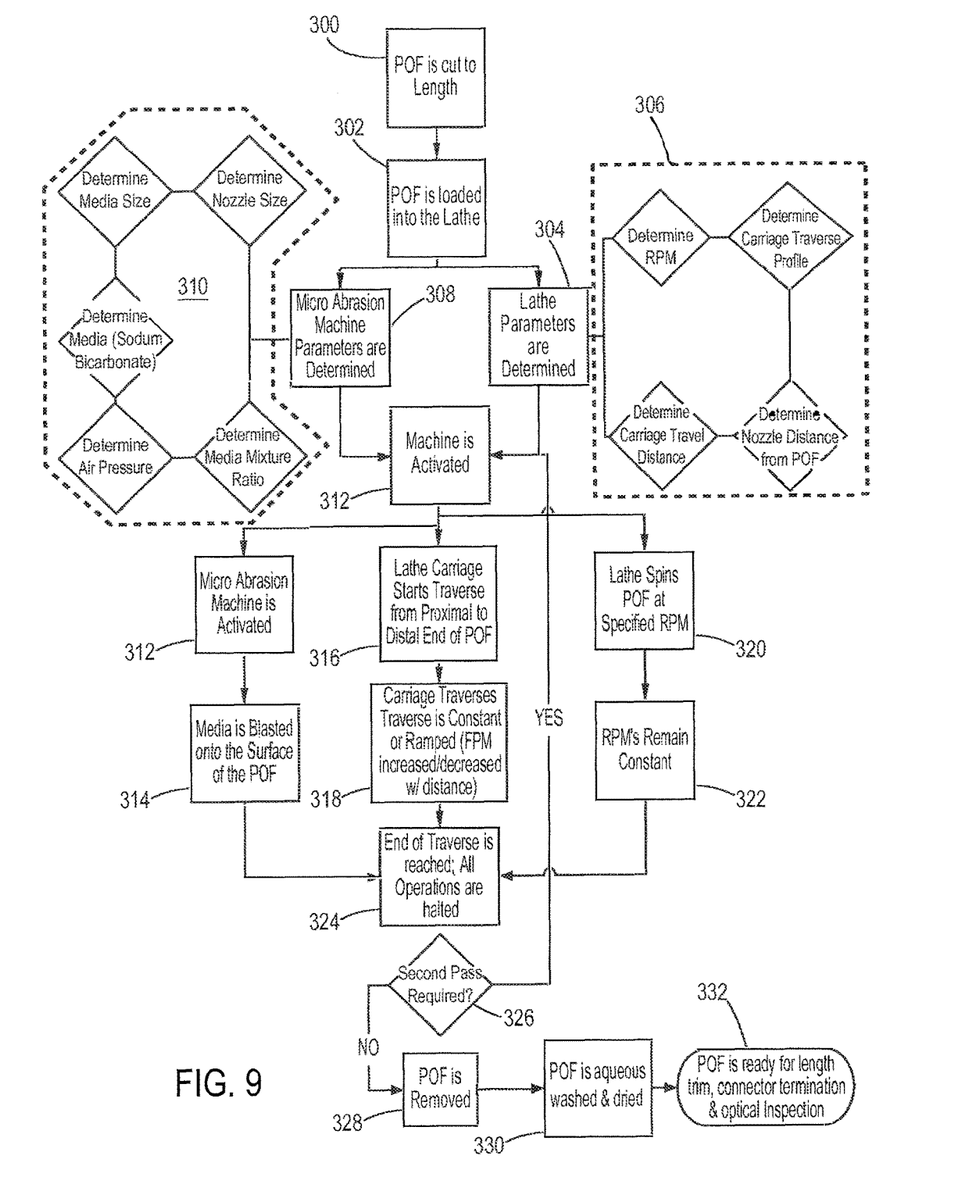
FIG. 9 illustrates a micro abrasion process flow for forming a side emission fiber, in accordance with aspects of the present disclosure.

FIG. 9 illustrates a micro abrasion process flow for forming a side emission optical fiber configured for use in the systems and devices described above. A piece of polymer optical fiber (POF) is first cut to a predetermined length at step 300 and then loaded into a lathe at step 302. The POF may be configured to have a core layer made of a suitable material, such as PMMA or polystyrene, with higher refractive indices of 1.49 and 1.59 respectively. A cladding layer may be provided made of a silicone resin, or a fluorinated polymer or perfluorinated polymer, for example, having a lower refractive index of approximately 1.46.

At step 304, the lathe parameters are determined, including, for example, the parameters shown in box 306 of RPM, carriage travel distance, carriage traverse profile, and a nozzle distance from the POF. At step 308 a number of parameters are determined and set for operation of the micro abrasion machine, including, for example, those shown at 310, which include determining nozzle size, media size, the media, air pressure, and media mixture ratio. In accordance with certain aspects of the present disclosure, a sodium bicarbonate media may be used. The media is used to remove the POF cladding and/or create micro porosity in the cladding and/or the core by being blasted at the surface of the POF.

With the micro abrasion machine parameters and the lather parameters set, the abrasion machine is activated at step 312. Concurrently, at steps 314, 318, and 324, respectively, the micro abrasion element activates, the lathe carriage starts a longitudinal traverse of the POF, and the lathe spins the POF at a specified RPM. As shown in step 316, the media is blasted onto the surface of the POF as the carriage traverses the POF at step 320 while the rotational speed of the lathe is maintained at step 322. The speed that the carriage traverses the POF may be controlled, e.g., maintained at a constant traverse speed, or an acceleration or deceleration of the carriage traverse speed may be introduced, depending on the desired properties of the finished POF.

Figure 10:
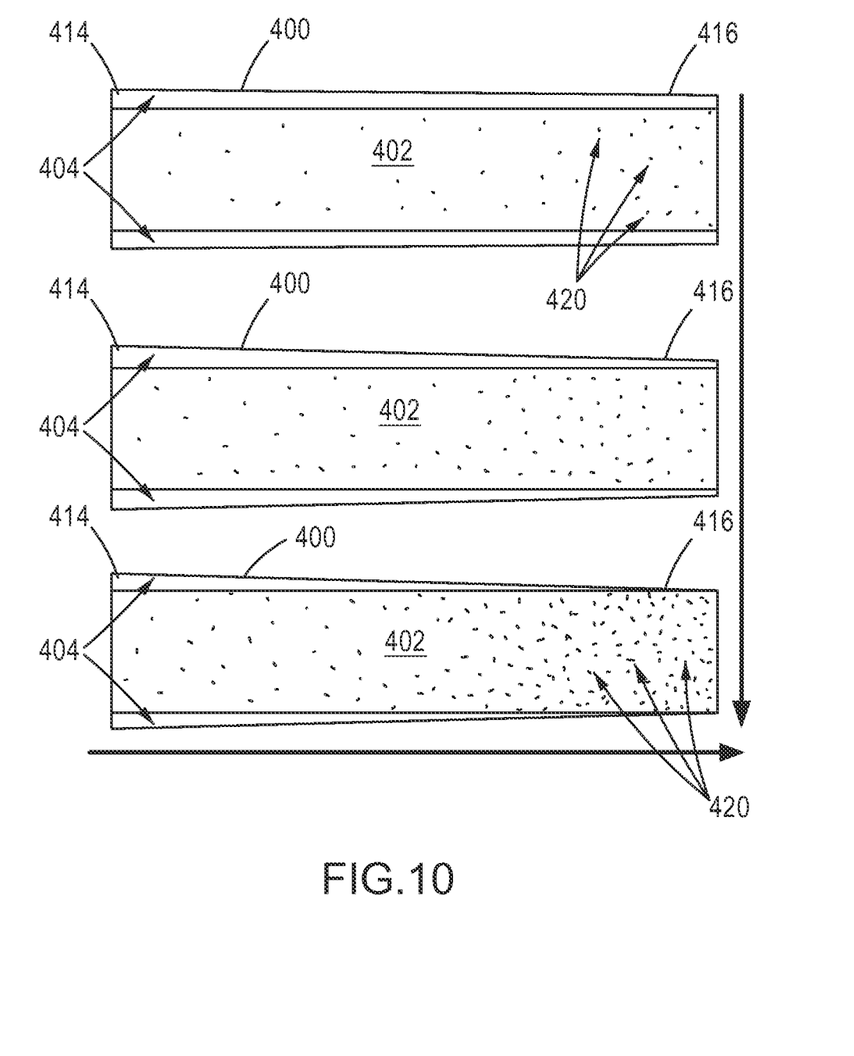
FIG. 10 illustrates various stages of a polymer optical fiber subjected to the micro abrasion process, in accordance with aspects of the present disclosure.

When the carriage reaches the end of the traverse at step 324, all operation of the micro abrasion machine is halted. FIG. 10 is a cross-sectional view of a POF 400 illustrating the core 402 and cladding 404 from a proximal end 414 to a distal end 416. The same POF 400 is shown three times to illustrate the impact of an increased number of abrasion passes and/or the blasting aggressiveness of a single pass on the thickness of the cladding 404. As the medium (e.g., sodium bicarbonate) is blasted onto the POF, the cladding 404 is slowly abraded. The blasted sodium bicarbonate removes some of the POF cladding 404 while also creating micro porosity within the cladding that remains. The rate of abrasion is dependent on the various parameters determined in steps 306 and 308, including but not limited to nozzle geometry, air pressure, media mixture, media size, RPM of the POF, carriage traverse rate and nozzle distance from the fiber. As illustrated by the arrow on the right, with increased number of abrasion passes and/or aggressiveness of a single pass, the cladding thickness decreases and the depth and frequency of porosity may increase from the proximal end 414 to distal end 416 of the POF 400. In addition, as the abrasion process begins, a small number of sodium bicarbonate particles may break entirely through the cladding 404 and facet the core 402. The core faceting 420 is illustrated in FIG. 10. The faceting on the core 402 may be increased by both quantity and depth pending the aggressiveness of the operation parameters and/or the number of abrasion passes. As the cladding 404 becomes thinner, the faceting effect on the core 402 increases.

Referring back to FIG. 9, a determination is made at step 326 whether to perform another abrasion pass. If a repeat pass is not necessary, the POF may be removed from the machine at step 328. At step 330, the POF is washed in an aqueous bath and dried. As shown in step 332, the washed and dried POF may be trimmed to a desired length. Optical fiber connectors, which may be FC, SC, ST, LC, MTRJ, or SMA type connectors, may be configured onto the POF. The side emission fiber may then undergo an optical inspection prior to being used as described above in one of the various devices.

Although described herein primarily with respect to an ultraviolet radiation source, the side emission fiber and method of making the same may be used with any wave generation source. For example, visible light may be used in a side emission fiber for effective cavity illumination during a medical procedure. The effectiveness of the side emission ensures 360° radial light emanation along a longitudinal length of the POF. Insertion of the POF through a trocar, for example, or in connection with a laparoscopic tool, provides a useful mechanism for surgeons to significantly enhance the visibility of a body cavity, for example, during a medical procedure. The substantial omnidirectional dispersion of light along the entire longitudinal length of the fiber floods the cavity with light, providing a substantial advantage over conventional light sources that provide limited directional lighting.

It is to be understood that any feature described in relation to any one aspect may be used alone, or in combination with other features described, and may also be used in combination with one or more features of any other of the disclosed aspects, or any combination of any other of the disclosed aspects.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. An ultraviolet irradiation system comprising:
a medical device having a central lumen;
an optical fiber having a longitudinal length, a proximal end, a distal end, and a cladding layer extending along the longitudinal length from the proximal end to the distal end;
and an ultraviolet wave generator, wherein ultraviolet waves generated by the wave generator are dispersed along the longitudinal length of the optical fiber to disinfect the central lumen of the medical device,
wherein a depth of porosity of the cladding layer increases along the longitudinal length of the optical fiber from the proximal end to the distal end.

2. The ultraviolet irradiation system of claim 1, wherein the medical device includes a cylindrical wall surrounding the central lumen, and the optical fiber is embedded into the wall.

3. The ultraviolet irradiation system of claim 1, wherein the optical fiber is embedded into the wall in a helical pattern.

4. The ultraviolet irradiation system of claim 1, wherein the optical fiber further comprises a cylindrical core, and wherein the cladding layer has a varied thickness over the longitudinal length.

5. The ultraviolet irradiation system of claim 4, wherein the core comprises a Poly(methyl methacrylate) (PMMA) material extruded with a specific proportion of scattering particles compounded into the PMMA material.

6. The ultraviolet irradiation system of claim 4, wherein surface pitting and solvent voids are formed in the cladding layer by a chemical abrasion process.

7. The ultraviolet irradiation system of claim 4, wherein surface pores are formed in the cladding layer by a micro abrasion process.

8. The ultraviolet irradiation system of claim 7, wherein facets in the core are formed by the micro abrasion process.

9. The ultraviolet irradiation system according to claim 1, wherein the medical device includes an endotracheal tube.

10. The ultraviolet irradiation system according to claim 1, wherein the medical device includes a central venous catheter stylet.

11. The ultraviolet irradiation system according to claim 1, wherein the medical device includes a foley catheter stylet.

12. The ultraviolet irradiation system according to claim 1, wherein the ultraviolet waves are uniformly emitted along the longitudinal length of the optical fiber.

13. The ultraviolet irradiation system of claim 1, wherein a thickness of the cladding layer decreases along the longitudinal length of the optical fiber from the proximal end to the distal end.

14. An ultraviolet irradiation system comprising:
a medical device having a central lumen;
an optical fiber having a longitudinal length, a proximal end, a distal end, and a cladding layer extending along the longitudinal length from the proximal end to the distal end, wherein a thickness of the cladding layer decreases along the longitudinal length of the optical fiber from the proximal end to the distal end, and wherein a depth of porosity of the cladding layer increases along the longitudinal length of the optical fiber from the proximal end to the distal end; and
an ultraviolet wave generator, wherein ultraviolet waves generated by the wave generator are dispersed along the longitudinal length of the optical fiber to disinfect the central lumen of the medical device.

15. The ultraviolet irradiation system according to claim 14, wherein the ultraviolet waves are uniformly emitted along the longitudinal length of the optical fiber.

16. The ultraviolet irradiation system of claim 14, wherein the optical fiber further comprises a cylindrical core comprising a Poly(methyl methacrylate) (PMMA) material having scattering particles compounded into the PMMA material.

* * * * *